United States Patent [19]

Glick

[11] Patent Number: 4,863,436
[45] Date of Patent: Sep. 5, 1989

[54] HYPODERMIC NEEDLE WITH PROTECTIVE COVER

[75] Inventor: Michael A. Glick, Denver, Colo.

[73] Assignee: Iatroban, Ltd., Chicago, Ill.

[21] Appl. No.: 255,721

[22] Filed: Oct. 11, 1988

Related U.S. Application Data

[63] Continuation of Ser. No. 116,389, Nov. 3, 1987, abandoned.

[51] Int. Cl.⁴ .............................................. A61M 5/32
[52] U.S. Cl. .................................... 604/198; 604/263
[58] Field of Search ................ 604/192, 187, 198, 263

[56] References Cited

U.S. PATENT DOCUMENTS

| | | | |
|---|---|---|---|
| 4,170,993 | 10/1979 | Alvarez . | |
| 4,425,120 | 1/1984 | Sampson et al. | 604/198 |
| 4,573,976 | 3/1986 | Sampson et al. | 604/198 |
| 4,631,057 | 12/1986 | Mitchell | 604/198 |
| 4,642,099 | 2/1987 | Phillips et al. | 604/136 |
| 4,664,654 | 5/1987 | Strauss | 604/198 |
| 4,693,708 | 9/1987 | Wanderer et al. | 604/198 |
| 4,695,274 | 9/1987 | Fox | 604/198 |
| 4,702,738 | 10/1987 | Spencer | 604/198 |

Primary Examiner—John D. Yasko
Attorney, Agent, or Firm—Welsh & Katz, Ltd.

[57] ABSTRACT

A hypodermic needle has a hub that is substantially equal in length to or longer than the length of the needle. A sliding cover, of the order of the length of the extended hub, is sized to make a sliding fit on the hub and to be supported by the hub when it slides. A detent in the inside of the cover engages a groove in the elongated hub that is axial and in the surface of the hub to guide the cover. In the alternative, the detent may be in the hub and the cover may be grooved. The groove has circumferential portions at either end to lock the sliding cover in a closed position to protect the needle point and in an open position to permit use of the needle as a hypodermic. An additional cover is provided which is adapted to engage the hub and envelope the sliding cover and needle.

32 Claims, 2 Drawing Sheets

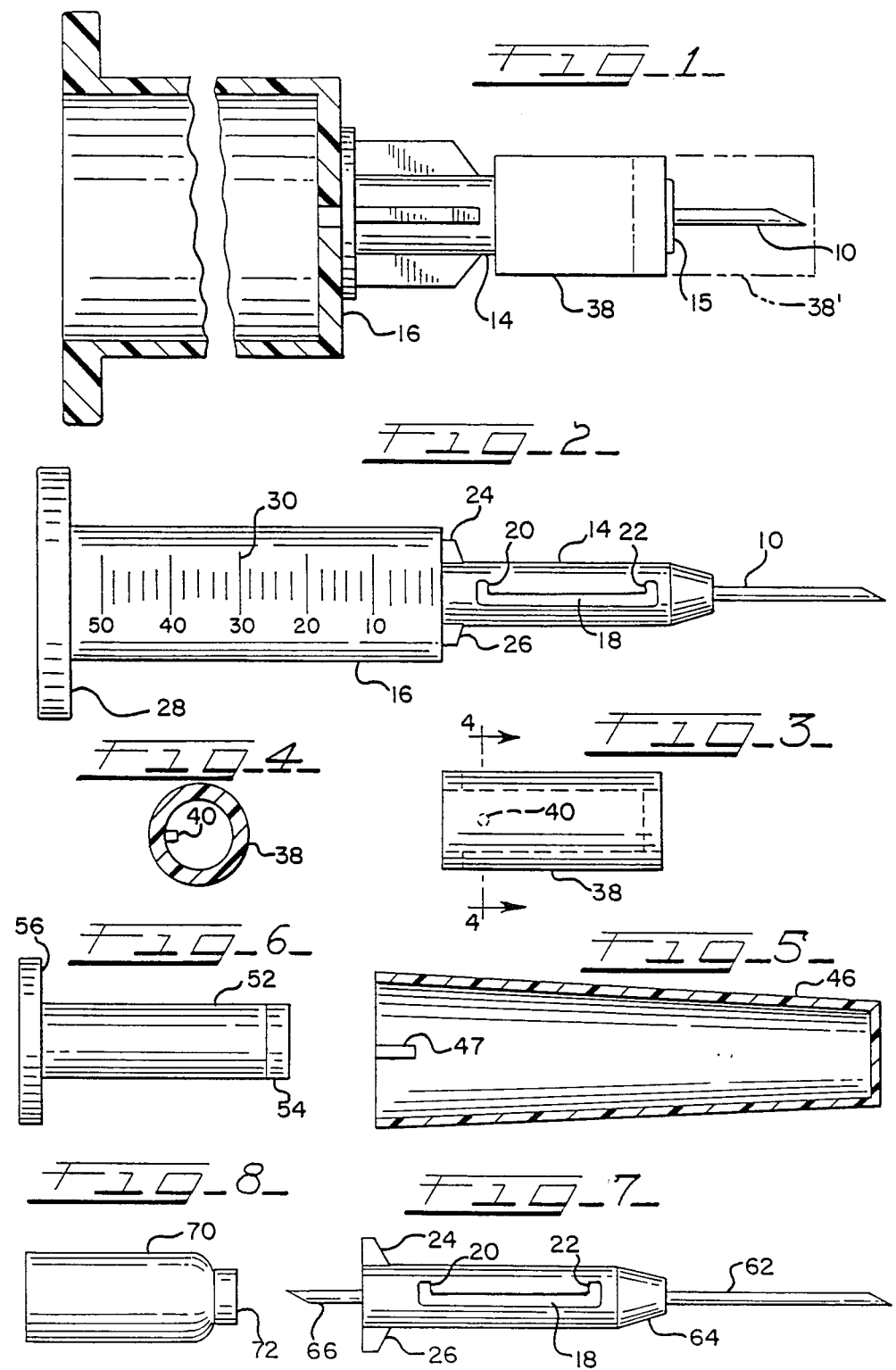

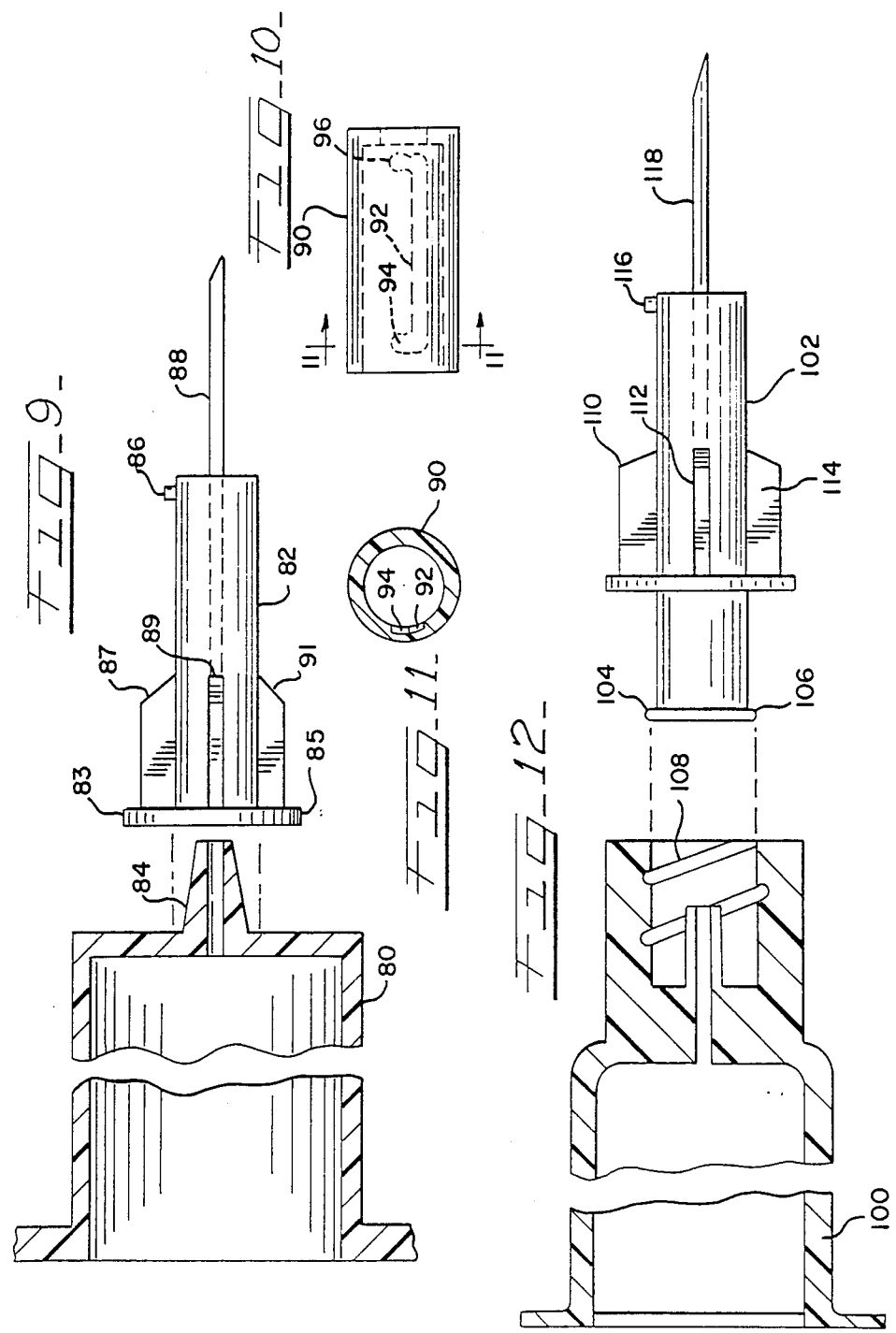

HYPODERMIC NEEDLE WITH PROTECTIVE COVER

CROSS-REFERENCE TO RELATED APPLICATION

This application is a continuation of my earlier application entitled "Hypodermic Needle with Protection Cover", having Serial No. 116,389 and a Filing Date of Nov. 3, 1987, which is now abandoned.

BACKGROUND OF THE INVENTION

This invention relates to hypodermic needles. In particular, it relates to the protection of people using syringes with needles to withdraw samples from the bodies of other people or animals or to inject materials into the bodies of other people or animals.

Health professionals and others who use hypodermic needles to inject medicine or other substances into the bodies of other people or to obtain samples of blood or other bodily fluids from people are subject to a risk of infection if they are stuck with a contaminated needle that has been withdrawn from an infected person. This is a matter of special concern when facing the possibility of dealing with people who have infectious hepatitis or acquired immune deficiency syndrome (AIDS), but it is preferable to avoid or minimize the possibility of infection with any disease. The needle in a hypodermic, being sharp to penetrate the skin readily for its intended purpose, is a threat to penetrate clothing and rubber gloves of the health professional using the hypodermic and thus to puncture the skin of the health professional. The threat of contamination is present with needles that are used for subcutaneous and intramuscular injection, but it is particularly threatening with needles used for intravenous injection of fluids and for the drawing of blood or other body fluids from veins or other parts of the body.

A hypodermic or hypodermic needle is here defined as a combination of a needle, a hub, and a syringe. The needle is attached to and passes through the hub, which in turn attaches to the syringe. If the hypodermic is designed for injection or withdrawal using positive pressure or vacuum produced by a plunger, then the needle is normally terminated after it has passed through the hub, and the syringe is designed to contain fluid and to make a sealed sliding engagement with the plunger. In this case, the plunger is an additional part of the combination representing the hypodermic, and the syringe is typically marked with graduations to measure quantities of fluids injected or withdrawn. If the hypodermic is designed for use in a vacuum withdrawal system, then the needle is normally double-ended, passing completely through the hub and extending beyond the hub in both directions. The syringe in this case does not contain fluid, but instead serves as a guide and support for a vacuum bottle with a soft plastic that is pierced by the needle to apply a vacuum to the needle when withdrawing samples. In either event, the hypodermic is normally equipped with a removable needle cover to protect health professionals from accidental contact with the point of the needle.

For any of the uses described above, universal practice is either to discard the needle after one use, or else to sterilize it before another use. This is done either by inserting the used needle in a cutting dispenser which cuts the needle from its hub and receives the cut needle, or by replacing the needle cover that was removed to ready the needle for use and removing the needle and hub from the body of the syringe to discard the combination of needle and cover. When the needle is inserted in a clipping device, the contaminated point is exposed between use of the needle and its insertion into the clipping dispenser. Carelessness on the part of the health professional or other user of the hypodermic, distractions occasioned by telephone calls and the like, or accidental jostling by passersby, all make it possible to bring the contaminated point of the needle into contact with the body of the health professional. A particular threat exists when the needle cover is replaced before the needle is discarded. In this case the health professional typically holds the needle cover in one hand and inserts the needle into an opening in the cover. The same distracting factors may cause the contaminated point of the needle to come into contact with his or her hand.

The threat described above has been the subject of several patents. Strauss, U.S. Pat. 4,664,654, "Automatic Protracting and Locking Hypodermic Needle Guard" is an example of one means for protecting the tip of a contaminated needle. Strauss teaches a sliding member that covers the needle. The sliding member can be locked in place to protect the point of the needle from coming in contact with anything. When the sliding member is unlocked, the tip of the needle and a portion of the needle are exposed for use. The sliding member is placed against the skin after the needle has made an initial penetration, and the sliding member is pushed back by the skin as the needle is inserted. The spring maintains force on the sliding member, and restores it to the protective position when the needle is withdrawn and the sliding member is removed from the surface of the skin. The sliding member is not locked in the open position. The device taught by Strauss has the disadvantages of being relatively complex mechanically, which increases its manufacturing cost, and also of coming in contact with the skin of a patient. This presents the possibility of contamination of the tip of the needle cover. In addition, the device taught by Strauss is adapted for subcutaneous and intramuscular use but would be difficult to use for intravenous injection or for the drawing of blood samples.

Mitchell, U.S. Pat. 4,631,057, is entitled "Shielded Needle". Mitchell teaches a shield that is concentric with and slides on the body of a syringe. When the shield is advanced to its farthest position in the direction of the needle, the needle is protected by the shield, which can be locked either in an open or closed position. A similar construction is taught by Sampson et al., U.S. Pat. 4,425,120, entitled "Shielded Hypodermic Syringe." The shield of Sampson et al. is locked by turning the shield to engage a detent in a slot. Each of these devices has the disadvantage of covering the body of the syringe when the needle is exposed, as it would be when the user of the syringe is drawing a measured quantity of medication from a vial. The necessity of reading volume marks through the shield represents a disadvantage of the constructions of Mitchell and Sampson et al.

SUMMARY OF THE INVENTION

It is an object of the present invention to provide an improved protective device for a needle in a hypodermic.

It is a further object of the present invention to provide an improved protective device for the needle in a hypodermic in which the device may be prevented from coming into contact with the body of a patient who is being injected.

It is a further object of the present invention to provide an improved protective cover for a needle of a hypodermic that does not interfere with the reading of volume marks on the syringe of the hypodermic.

It is a further object of the present invention to provide an improved protective device for a hypodermic that is used for subcutaneous injection.

It is a further object of the present invention to provide an improved protective device for a hypodermic that is used to give intramuscular injections.

It is a further object of the present invention to provide an improved protective cover for a hypodermic that is used to provide intravenous injections.

It is a further object of the present invention to provide an improved protective device for a hypodermic that is used to withdraw blood from the vein of a patient.

It is a further object of the present invention to provide an improved protective cover for a hypodermic that is inexpensive and easy to manufacture.

These and other objects of the invention are achieved by providing a hypodermic having a hub that is substantially equal in length to or longer than the length of the needle. A sliding cover, of the order of the length of the extended hub, is sized to make a sliding fit on the hub and to be supported by the hub when it slides. A detent in the inside of the cover engages a groove in the elongated hub that is axial and in the surface of the hub to guide the cover. In the alternative, the detent may be in the hub and the cover may be grooved. The groove has circumferential portions at either end to lock the sliding cover in a closed position to protect the needle point and in an open position to permit use of the needle as part of a hypodermic.

BRIEF DESCRIPTION OF THE DRAWINGS

FIG. 1 is a side view of a hypodermic with a protective cover for the practice of the present invention.

FIG. 2 is a side view of a hypodermic for the practice of the present invention.

FIG. 3 is a side view of the sliding collar of the present invention.

FIG. 4 is an end view of the sliding collar of FIG. 3.

FIG. 5 is a side view of a protective cover for the hypodermic of the present invention.

FIG. 6 is a plunger for use with the hypodermic of FIG. 2.

FIG. 7 is a double-ended needle for use with a syringe similar to the syringe of FIG. 2.

FIG. 8 is a vacuum bottle for the drawing of samples from a subject using the double-ended needle of FIG. 7.

FIG. 9 is a sectional view of a syringe and needle.

FIG. 10 is a side view of a protective collar.

FIG. 11 is an end view of the protective collar of FIG. 10.

FIG. 12 is a sectional side view of a syringe and needle.

DETAILED DESCRIPTION OF THE PREFERRED EMBODIMENT

FIG. 1 is a side view of a hypodermic with a protective cover. In FIG. 1, a needle 10 is attached to a hub 14 which in turn is attached to a syringe 16. A protective cover in the from of a collar 38 is withdrawn onto the hub 14, exposing all of the needle 10 and a portion 15 of the hub 14. Thus, as seen in FIG. 1, the protective cover 38 is shorter than the hub. This assures that the collar 38 will not be in contact with a subject that is being injected by the needle 10. Before and after use, the needle 10 and the portion 15 are protected from contact with a health professional or other user of the needle by sliding the collar 38 into the protected position 38', which is shown in phantom. Thus, as seen in FIG. 1, the protective cover 38 is longer than the needle.

FIG. 2 is a side view of a hypodermic needle for the practice of the present invention with protective cover 38 removed. In FIG. 2, the needle 10 passes through the hub 14 that is threaded into or pressed onto the syringe 16. The hub 14 is made to be substantialy equal to or greater than the exposed length of the needle 10. A groove 18 in the hub 14 runs axially for most of the length of the hub 14 and includes circumferential groove portions 20 and 22 at its extremities. Projections 24 and 26 engage and retain an additional needle cover 46 (shown in FIG. 5). The syringe 16 includes a collar 28 which represents a finger stop for the operator when the syringe 16 is being used to withdraw fluids from a subject. Graduations 30 measure the amount of fluid in the syringe 16.

FIG. 3 is a side view of the collar 38 and FIG. 4 is an end view of the collar 38 which is sized to fit over the hub 14 of FIG. 1 and to slide on the hub 14. A detent 40 projects inside the collar 38 to engage the groove 18 and the circumferential portions 20 and 22 of FIG. 2 when the collar 38 is placed on the hub 14. When the collar 38 is disposed with the detent 40 in the circumferential portion 20 of FIG. 2, the collar 38 is retracted and the needle 10 is exposed for use. When the detent 40 is in the circumferential portion 22, the collar 38 is advanced to cover the needle 10, protecting the user of the syringe 16 from accidental contact with the needle 10. Since the collar 38 may be retracted onto the hub 14 so as to expose all of the needle 10 and portion 15 of the hub, the collar 38 may be kept from touching the body of a patient. This is an additional protective factor for the health professional to minimize the possibility of contamination from bodily fluids of the patient or subject.

FIG. 5 is a sectional side view of a needle cover 46 that is placed over the needle 10 and the hub 14 of FIG. 1. The needle cover 46 fits onto and is retained by friction against the projections 24 and 26 of FIG. 2. A detent 47 engages one of the projections 24 and 26 to prevent the needle cover 46 from rotating with respect to the hub 14 when the needle cover 46 is rotated about its axis to screw the hub 14 into or onto the syringe 16. Without the present invention, the health professional using the syringe 16 would remove the needle cover 46 to use the syringe 16. After use, the health professional would hold the needle cover 46 in one hand while inserting the needle 10 into the needle cover 46. This is the operation that presents the greatest risk that the health professional will be stuck by the needle 10. This risk is eliminated when the collar 38 of FIGS. 3 and 4 is slid into the protective position, with the detent 40 in the circumferential portion 22. The needle cover 46 can then be replaced without risk of injury to the health professional or other user.

FIG. 6 is a side view of a plunger 52. The plunger 52 includes a piston 54 which makes a sealing contact with the inside of the syringe 16 to draw measured amounts of liquid into the syringe 16 and inject those measured amounts subcutaneously, intramuscularly or intravenously. An enlarged thumb plate 56 provides a place for the operator to pull or press. An alternative method of using the syringe of FIG. 2 is indicated with the needle 62 of FIG. 7 which is connected to a hub 64 and continues into an internal needle 66. The combination of FIG. 7 is used together with a bottle 70 of FIG. 8 which is produced with an internal vacuum that is sealed by a resilient seal 72 that can be pierced by the needle 66 to apply suction to the needle 62. The needle 66 is a continuous extension of the needle 62, passing through the hub 64. This is a use typical of a blood sampling system sold under the registerd trademark VACUTAINER. The combination of FIGS. 7 and 8 is often used with a syringe similar to the syringe 16 to take samples of blood from veins or other bodily fluids from other locations in the body. The needle 62 of FIG. 7 is protected by the collar 38 of FIGS. 3 and 4 in the same way as the needle 10 of FIGS. 1 and 2.

The sliding collar of FIGS. 3 and 4 thus provides protection to the user of the syringe 16 against accidental contact with either the needle 10 or the needle 62. After use, the user may replace the needle cover 46, unscrew the needle form the syringe 16 and discard it.

The examples shown so far represent needles that are fixed to a syringe which is either a container of a fluid to be injected or is a support for the vacuum bottle 70 of FIG. 8. The invention is also adaptable to other commonly used forms of needles. FIG. 9 is a sectional side view of a syringe 80 that is connectible to a hub 82 by a tapered insert 84. The hub 82 has a detent 86 that is designed for the practice of the present invention to protect health professionals and others from the exposed end of the needle 88. Projections 87, 89 and 91 retain the cover 46 of FIG. 5.

FIGS. 10 and 11 show a collar 90 that shields the exposed end of the needle 88. FIG. 10 is a side view and FIG. 11 is an end view of the collar 90 that includes an internal groove 92 that engages the detent 86 of FIG. 9. The groove 92 runs axially on the inside of the collar 90. A first locking portion 94 of the groove 92 locks the collar 90 in a protective position, and a second locking portion 96 of the groove 92 locks the collar 90 in an operating position, out of the way to enable the user to give an injection or withdraw a sample. As before, the syringe 80 of FIG. 9 may contain fluid to be injected by means such as the plunger 52 of FIG. 6. Alternatively the syringe 80 may contain a plunger 52 which is used to withdraw fluids from the body.

The tapered insert 84 of FIG. 9 represents one way of attaching a hub 82 to a syringe 80. Another means of attaching such a hub is shown in FIG. 12, in which a syringe 100 engages a hub 102. Two ears 104 and 106 screw into threads 108 to secure the hub 102 to the syringe 100. Three projections 110, 112 and 114 in the hub 102 engage the cover 46 of FIG. 5. A detent 116 is shown on the hub 102. The hub 102 is thus adapted for use with the grooved collar 90 of FIGS. 10 and 11. If, instead, the hub 102 had been grooved like the hub 14 of FIG. 1, then the collar 38 of FIG. 3 could have been used to protect the needles 88 of FIG. 9 and 118 of FIG. 12.

Various alternative modes of practicing the invention are possible. For example, the grooves 18 of FIG. 2 and 92 of FIGS. 10 and 11 may be helical rather than longitudinal as shown. The circumferential portion 22 of the groove 18 of FIG. 2 may extend longitudinally to the end of the hub 14 to permit ready assembly of the collar 38 on the hub 14. The same is true of the locking portion 96 of FIG. 10. The needles 88 of FIG. 9 and 118 of FIG. 12 are shown as terminating inside the hubs 82 and 102 respectively. They could equally as well extend through the hubs 82 and 102 to function as part of a vacuum sampling system such as the VACUTAINER system. The hubs 14, 82 and 102 are shown in the preferred embodiment as right circular cylinders. However, they could have any form of cylindrical symmetry, permitting axial motion of a cover with matching symmetry.

The description of specific embodiments of the present invention is intended to set forth the best mode known to the inventor for the practice of the invention. It should be taken as illustrative and not as limiting, and the scope of the invention should be limited only by the appended claims.

What is claimed is:

1. A protective system for a hypodermic needle of a predetermined exposed length for injecting fluids into a subject or withdrawing fluids from the subject, the protective system comprising:
   a hub containing a hypodermic needle, said hub being substantially coaxial with the needle and having a length greater than the exposed length of the needle;
   a protective cover slidably mounted on said hub, having a length greater than the exposed length of the needle and shorter than the hub length, and including an aperture sized to pass the needle;
   means for maintaining the protective cover in a protective position that shields the needle;
   means for maintaining the protective cover in an operative position that exposes a portion of the hub and all of the exposed length of the needle for hypodermic use; and
   means for permitting movement of the protective cover between the protective position and the operative position.

2. The protective system of claim 1 wherein the means for maintaining the protective cover in a protective position comprises a detent on the hub that engages a substantially circumferential groove in the protective cover.

3. The protective system of claim 1 wherein the means for maintaining the protective cover in a protective position comprises a detent on the protective cover that engages a substantially circumferential groove in the hub.

4. The protective system of claim 1 wherein the means for maintaining the protective cover in an operative position comprises a detent on the hub that engages a substantially circumferential groove in the protective cover.

5. The protective system of claim 1 wherein the means for maintaining the protective cover in an operative position comprises a detent on the protective cover that engages a substantially circumferential groove in the hub.

6. The protective system of claim 1 wherein the means for permitting movement of the protective cover between the protective position and the operative position comprises a groove connecting the means for maintaining the cover in each position.

7. The protective system of claim 6 wherein the groove is substantially longitudinal.

8. The protective system of claim 6 wherein the groove is helical.

9. A protective system to minimize accidental contact with the tip of a hypodermic needle used for injecting fluids into or withdrawing fluids from a subject, the system comprising:
- an elongated hub supporting a hypodermic needle and mounted on the body of a syringe, the hub having a length greater than the needle length, and the hub exhibiting an external cylindrical shape along an axis substantially coincident with the needle;
- a cover mounted on the hub, having a length greater than the needle length and shorter than the hub length, and having an internal portion that exhibits cylindrical symmetry substantially identical to the external shape of the hub so that the cover has a sliding fit with the hub in the direction of the axis;
- a groove in the surface of the hub with a longitudinal portion that extends along most of the elongated hub and is terminated at a first end by a first circumferential portion and at a second end by a second circumferential portion, the combination of the longitudinal portion and the circumferential portions representing a single continuous groove; and
- a detent in the internal portion of the cover that is sized to engage the groove in the hub to permit the cover to be locked in an operating position fully exposing the hypodermic needle, or a protective position fully covering the length of the hypodermic needle, or to be slid between the operating position and the protective position.

10. A hypodermic syringe, suitable for use in withdrawing bodily fluids from a subject or injecting fluids into a subject, which comprises in combination:
 (a) a syringe hollow body member having an open first end and a closed second end containing a fluid aperture;
 (b) a syringe plunger mounted in said hollow body member at said first end;
 (c) an elongated syringe hub mounted on said hollow body member second end over said fluid aperture and having a forward end spaced from said second end;
 (d) a hypodermic needle mounted in said hub forward end in fluid communication with said fluid aperture in said hollow body member second end, and having an exposed length which is shorter than the hub length projecting forward of said hub;
 (e) a protective needle cover slidably mounted on said elongated hub, having a length greater than the exposed length of the mounted needle and shorter than the length of the hub, and having a forward end including an aperture sized to pass the needle;
 (f) means for maintaining the protective cover in a protective position that shields the exposed needle length;
 (g) means for maintaining the protective cover in an operative position that exposes a portion of the hub and all of the exposed needle length for hypodermic use; and
 (h) means for permitting movement of the protective cover between the protective position and the operative position.

11. The hypodermic syringe of claim 10 wherein the means for maintaining the protective cover in a protective position comprises a detent on the hub that engages a substantially circumferential groove in the protective cover.

12. The hypodermic syringe of claim 10 wherein the means for maintaining the protective cover in a protective position comprises a detent on the protective cover that engages a substantially circumferential groove in the hub.

13. The hypodermic syringe of claim 10 wherein the means for maintaining the protective cover in an operative position comprises a detent on the hub that engages a substantially circumferential groove in the protective cover.

14. The hypodermic syringe of claim 10 wherein the means for maintaining the protective cover in an operative position comprises a detent on the protective cover that engages a substantially circumferential groove in the hub.

15. The hypodermic syringe of claim 10 wherein the means for permitting movement of the protective cover between the protective position and the operative position comprises a groove connecting the means for maintaining the cover in each position.

16. The hypodermic syringe of claim 15 wherein the groove is substantially longitudinal.

17. The hypodermic syringe of claim 15 wherein the groove is helical.

18. The hypodermic syringe of claim 10 further comprising a second cover for confining said exposed needle length, said elongated hub, and said slidable protective cover, and including means for removable attachment of said second cover to said hypodermic syringe.

19. The hypodermic syringe of claim 18 wherein said removabe attachment means includes a radial projection on said elongated hub at said hollow body member second end and means on said second cover for engaging said radial projection.

20. The hypodermic syringe of claim 19 comprising a detent element in said second cover for preventing said second cover from rotating with respect to said hub.

21. The hypodermic syringe of claim 10 wherein said hub is detachably mounted on said hollow body member second end.

22. A hypodermic needle assembly, suitable for use in withdrawing bodily fluids from a subject, which comprises in combination;
 (a) an elongated hub having a forward end and an after end;
 (b) a forward hypodermic needle mounted in the forward end of said hub and having an exposed length projecting forward of said hub which is shorter than the hub length;
 (c) an after hypodermic needle mounted in the after end of said hub in fluid communication with said forward hypodermic needle, for passing bodily fluids from a subject penetrated by said forward needle into a vacuumized receptacle;
 (d) a protective needle cover slidably mounted on said elongated hub, having a length greater than the exposed length of the forward needle and shorter than the length of the hub, and having a forward end including an aperture sized to pass said forward needle;
 (e) means for maintaining the protective cover in a protective position that shields the exposed length of said forward needle;
 (f) means for maintaining the protective cover in an operative position that exposes a portion of the hub and all of the exposed length of the forward needle for hypodermic use; and (g) means for permitting movement of the protective cover between the protective position and the operative position.

23. The hypodermic needle assembly of claim 22 wherein the means for maintaining the protective cover in a protective position comprises a detent on the hub that engages a substantially circumferential groove in the protective cover.

24. The hypodermic needle assembly of claim 22 wherein the means for maintaining the protective cover in a protective position comprises a detent on the protective cover that engages a substantially circumferential groove in the hub.

25. The hypodermic needle assembly of claim 22 wherein the means for maintaining the protective cover in an operative position comprises a detent on the hub that engages a substantially circumferential groove in the protective cover.

26. The hypodermic needle assembly of claim 23 wherein the means for maintaining the protective cover in an operative position comprises a detent on the protective cover that engages a substantially circumferential groove in the hub.

27. The hypodermic needle assembly of claim 23 wherein the means for permitting movement of the protective cover between the protective position and the operative position comprises a groove connecting the means for maintaining the cover in each position.

28. The hypodermic needle assembly of claim 27 wherein the groove is substantially longitudinal.

29. The hypodermic needle assembly of claim 27 wherein the groove is helical.

30. The hypodermic needle assembly of claim 22 further comprising an outer cover for confining said exposed needle length of said forward needle, said elongated hub, and said slidable protective needle cover, and including means for removable attachment of said outer cover to said hypodermic needle assembly.

31. The hypodermic needle assembly of claim 30 wherein said removable attachment means includes a radial projection on said elongated hub at said after end and means on said syringe cover for engaging said radial projection.

32. The hypodermic needle assembly of claim 22 wherein said after hypodermic needle is a continuous extension of said forward hypodermic needle.

* * * * *

UNITED STATES PATENT AND TRADEMARK OFFICE
CERTIFICATE OF CORRECTION

PATENT NO. : 4,863,436
DATED : September 5, 1989
INVENTOR(S) : Michael A. Glick

It is certified that error appears in the above-identified patent and that said Letters Patent is hereby corrected as shown below:

IN THE SPECIFICATION:

In Column 5, Line 13, "registerd" should be --registered--.

In Column 5, Line 24, "form" should be --from--.

IN THE CLAIMS:

In Column 8, Line 31, "removabe" should be --removable--.

In Column 9, Line 19, "claim 23" should be --claim 22--.

In Column 10, Line 1, "claim 23" should be --claim 22--.

Signed and Sealed this

Sixteenth Day of April, 1991

Attest:

HARRY F. MANBECK, JR.

*Attesting Officer*       *Commissioner of Patents and Trademarks*